United States Patent
Callaghan

[11] Patent Number: 6,162,401
[45] Date of Patent: Dec. 19, 2000

[54] CYTOFUNNEL ARRANGEMENT

[75] Inventor: Karl J. Callaghan, Lucan, Ireland

[73] Assignee: Shandon Scientific Limited, Cheshire, United Kingdom

[21] Appl. No.: 09/082,573

[22] Filed: May 21, 1998

[30] Foreign Application Priority Data

May 23, 1997 [GB] United Kingdom .................... 9710773

[51] Int. Cl.[7] ................................. B01L 9/00; G01N 9/30
[52] U.S. Cl. ............................ 422/104; 422/72; 422/100; 422/103; 436/45; 436/46; 436/174; 436/180
[58] Field of Search ............................. 422/104, 72, 103, 422/100; 436/45, 46, 174, 180

[56] References Cited

U.S. PATENT DOCUMENTS

| | | | |
|---|---|---|---|
| 4,265,762 | 5/1981 | Brenholt | 210/321.1 |
| 4,327,661 | 5/1982 | Boeckel | 118/52 |
| 4,344,562 | 8/1982 | Ricci | 233/26 |
| 4,357,240 | 11/1982 | Mehra et al. | 210/455 |
| 4,391,710 | 7/1983 | Gordon | 210/361 |
| 4,853,188 | 8/1989 | Toya | 422/104 |
| 5,137,710 | 8/1992 | Smalley et al. | 424/3 |
| 5,272,093 | 12/1993 | Sliva et al. | 436/180 |
| 5,380,435 | 1/1995 | Stokes et al. | 210/361 |
| 5,589,400 | 12/1996 | Hayes | 436/177 |
| 5,830,413 | 11/1998 | Lang et al. | 422/100 |
| 5,908,665 | 11/1999 | Childress | 156/92 |
| 5,952,239 | 9/1999 | Hayes et al. | 436/177 |

FOREIGN PATENT DOCUMENTS

| | | |
|---|---|---|
| 0 184 374 | 12/1984 | European Pat. Off. . |
| 61-234337 | 10/1986 | Japan . |

*Primary Examiner*—Long V. Le
*Assistant Examiner*—Kathryn Bex
*Attorney, Agent, or Firm*—Fulwider Patton Lee & Utecht

[57] ABSTRACT

A cytofunnel arrangement, for use in preparation of slides for microscopic examination, comprises in combination, a specimen funnel 14, a microscope slide 12 and a slide holder 10 which holds the slide against a port 36 in a base portion of the specimen funnel 14, the slide holder being integrally connected with the specimen funnel and being adapted for destructive separation from the specimen funnel along predetermined lines or regions to allow extraction of the slide 12 undamaged. The specimen funnel and the slide holder may be of compatible plastics and may be connected by adhesive or may be welded together. A tear strip or separation filament 50 located between the specimen funnel and slide holder may be provided to assist separation of the two components. The tear strip 50 may be formed by an electrical resistance wire utilized initially to bond the specimen funnel and slide holder together by electrofusion welding.

3 Claims, 2 Drawing Sheets

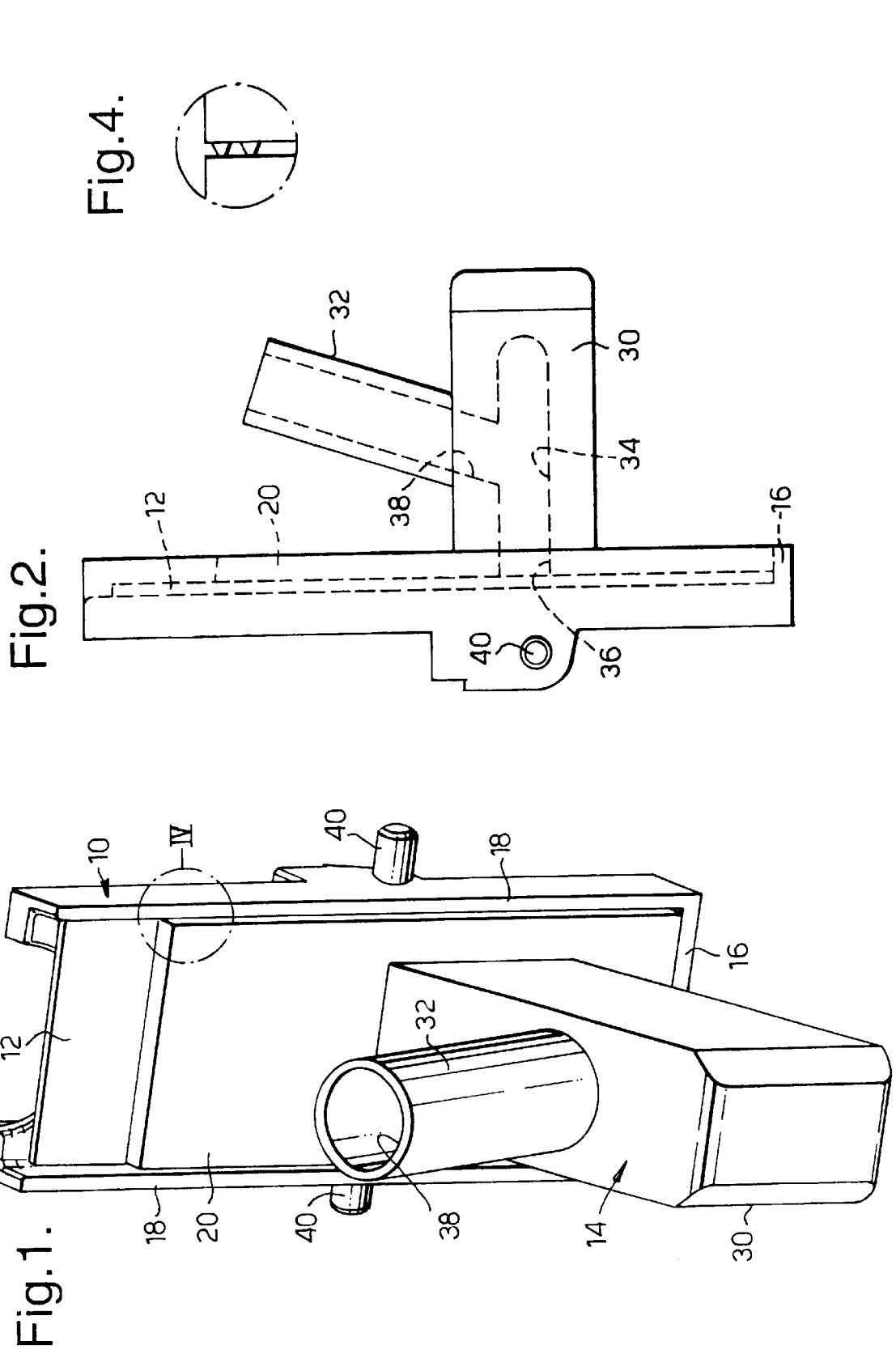

CYTOFUNNEL ARRANGEMENT

THIS INVENTION relates to a cytofunnel arrangement, as defined below, of the kind used, for example, in the preparation, for microscopic examination, of cells or other solid material originally present in suspension in liquid samples, such as pathological medical samples, for example body fluids, such as cerebrospinal fluid. In such preparation, it is generally desired to obtain a relatively dense distribution of cells or other particles, over a viewing area on the surface of a glass slide, i.e. a microscope slide, from a liquid sample in which such cells or particles may be relatively sparsely distributed throughout the sample in suspension in the sample. One known way of achieving this desired result is to place, the liquid sample concerned in a cytofunnel arrangement in which the glass slide forms a base of a compartment and to mount this cytofunnel arrangement in a centrifuge, generally together with a plurality of similar cytofunnel arrangements, and to operate the centrifuge, whereby the cells or other solid particles initially in suspension in the liquid sample are caused to deposit rapidly, under extreme centrifugal force, onto the glass slide. Such a procedure is referred to generally, and herein, as cytocentrifugation.

The term "cytofunnel arrangement" as used herein denotes the combination of (a) a specimen funnel including a conduit terminating at a first end in an opening for the introduction of a liquid specimen and at a second end in an outlet or port in a base portion of the specimen funnel, (b) a microscope slide and (c) a slide holder which serves to hold the slide against the base portion of the specimen funnel so that the slide extends across and occludes said outlet or port of said conduit of the specimen funnel.

A known cytofunnel arrangement comprises a plurality of distinct components, one of which comprises the specimen funnel, another of which components comprises the slide itself, and a still further component of which comprises said slide holder, the slide holder being detachably securable, for example by means of spring clips, to the specimen funnel, with the slide located in the slide holder in a predetermined position and orientation and in engagement with said base surface of the specimen funnel.

Cytofunnel arrangements of this type, and their use in conjunction with cytocentrifuges, are disclosed, for example, in EP 0184374 and EP 0047840, to which reference should be had.

Known cytofunnel arrangements of this type are intended to be reusable, and to be assembled manually for each centrifugation and to be carefully disassembled after each centrifugation, with the slide being passed to further processing, e.g. fixing, staining, etc. Whilst the specimen funnel and slide holder are washed and sterilized ready for assembly around a fresh slide, in preparation for centrifugation of a further sample.

It is an object of the present invention to provide an improved cytofunnel arrangement which requires less preparation at the point of use by personnel than is the case with known cytofunnel arrangements and which is consequently less prone to incorrect use.

According to one aspect of the present invention, there is provided a cytofunnel arrangement, as herein defined, comprising a specimen funnel, a slide and a slide holder, the slide holder being integrally connected with the specimen funnel and being adapted for separation from the specimen funnel along predetermined lines or regions to allow extraction of the slide undamaged.

An embodiment of the invention is described below by way of example with reference to the accompanying drawings, in which:

FIG. 1 is a perspective view of a cytofunnel arrangement in accordance with the invention;

FIG. 2 is a side elevation view of the cytofunnel arrangement of FIG. 1;

FIG. 4 is a view to an enlarged scale of the portion of FIG. 1 indicated at IV.

Figure 5:
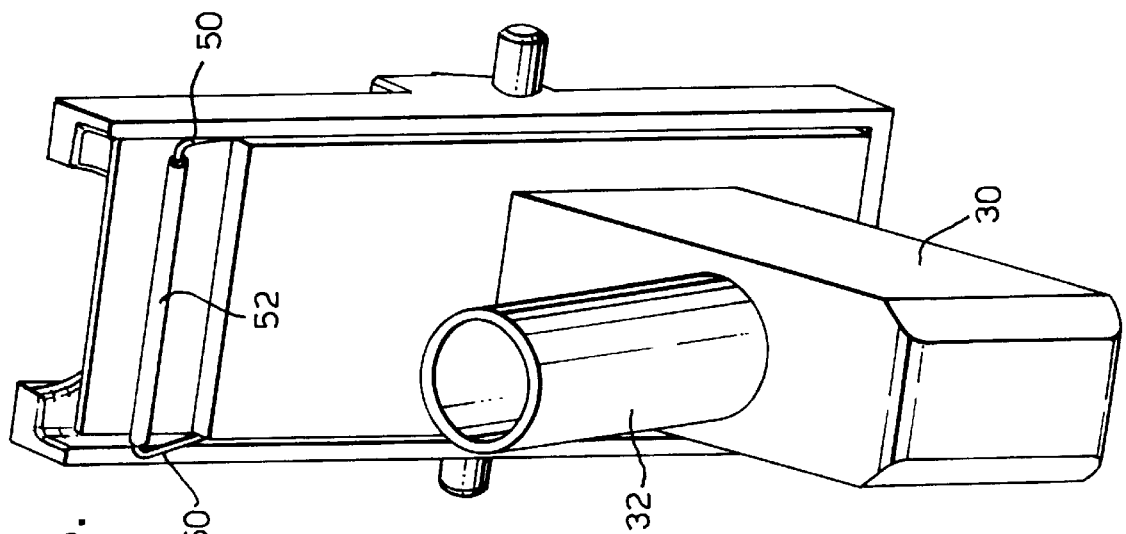
FIG. 5 is a perspective view similar to FIG. 1, illustrating a variant.
Figure 3:
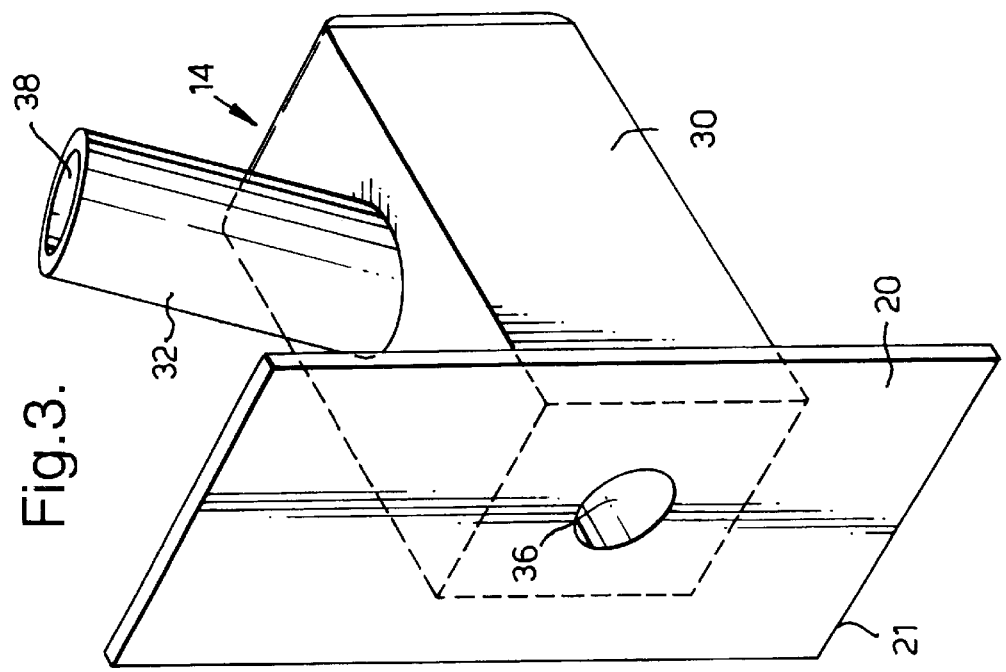
FIG. 3 is a perspective view of the specimen funnel portion of the arrangement.

The cytofunnel arrangement described below with reference to FIGS. 1 to 4 comprises three principal parts, namely a slide holder 10 of thermoplastics material such as polypropylene, a conventional glass microscope slide 12 and a specimen funnel 14, of the same thermoplastics material as slide holder 13 or of a compatible thermoplastics material, the slide being held between the slide holder and the specimen funnel. Whereas in conventional cytofunnel arrangements, the slide holder and the specimen funnel are held together releasably by spring clips and are intended for repeated re-assembly and re-use with successive microscope slides after necessary cleaning and sterilizing and so on, the cytofunnel arrangement to be described below with reference to FIGS. 1 to 4 is a disposable, single use assembly which is supplied fully assembled by the manufacturer. Whilst it is envisaged that the assembly of FIGS. 1 to 4 will be supplied by the manufacturer in individual sterile packaging, larger quantities may be supplied loosely packed in quantities of 50 or more. The assembly is used once and is then disposed of. The slide holder 10 is preferably formed as a unitary plastics injection moulding and the specimen funnel 14 is likewise preferably formed as a unitary plastics section moulding. (The slide holder and funnel may, of course, be formed, instead, by some other process such as blow moulding). The slide holder 10 and funnel 14 are fixed together positively, for example by welding. In keeping with their single use, disposable, character, the plastics components 10 and 14 are designed to be manufactured cheaply, consistent with adequate strength and fitness for their purpose. As described in greater detail below, the technique used for securing the parts 10 and 14 together is such that, after the cytofunnel arrangement has been used for cytocentrifugation of a sample, the specimen funnel can readily and controllably be separated from the slide holder, to allow extraction of the slide without risk of damage to the latter.

Referring to the drawings, the slide holder 10 takes the form of a shallow tray including a base providing a flat supporting surface for the slide 12 and having an end wall 16 and opposite side walls 18 extending generally perpendicular to that flat supporting surface, past, respectively, an end edge and opposite side edges of the slide 12 thereby to locate and accurately retain in position the glass slide 12. The specimen funnel 14 includes a portion 20 in the form of a flat rectangular plate of a width to fit closely between the portions of the opposing side walls 18 which extend beyond the slide 12. The slide 12 is sandwiched between the base of the tray portion of the slide holder and the plate portion 20, the lower edge 21 of plate portion 20 engaging the end wall 16. The assembly is held together by welding the lateral edges of portion 20 to the opposing surfaces of side walls 18. As illustrated, the upper end of plate portion 20 preferably stops short of the upper edge of slide 12 and the upper edge of the slide holder base is cut away or recessed, as best shown in FIG. 1, to allow access for a finger and thumb to grasp the upper end of the slide during extraction of the slide as described below.

The specimen funnel 14 comprises a block 30 extending generally perpendicularly from the plate portion 20 on the face of the latter which faces away from the slide holder 10 and slide 12, and a hollow funnel portion 32 which extends upwardly and at an angle from the upper surface of block 30 as shown in FIG. 2. As illustrated in broken lines in FIG. 2, a conduit within the specimen funnel includes a bore 34 which extends within block 30 perpendicular to the plate portion 20, from an opening or port 36 (see FIG. 3) in the face of plate 20, the bore 34 being, in the arrangement shown in FIGS. 1 to 4, closed at its opposite end and intersected partway along its length by a bore 38 which forms, an extension, within the block 30, of the internal passageway within the funnel portion 32, which passage terminates at its upper end in an open mouth funnel.

The slide holder 10 has, on either side, a respective cylindrical boss or stub shaft 40 formed integrally with the remainder of slide holder 10 and coaxial with the stub shaft on the opposite side. These stub shafts 40 serve for the pivotal mounting of the cytofunnel arrangement in the centrifuge (not shown) in substantially the same way as described in EP 0184374 and EP 0047840 referred to above, such pivotal mounting, as also described in EP 0184374 and EP 0047840, allowing the cytofunnel arrangement, when mounted in its centrifuge, but with the centrifuge at rest, to adopt an orientation, about the pivot axis defined by shafts 40, such that the bore 34 is inclined downwardly away from port 36 so that a liquid sample introduced into the funnel via bore 38 in funnel portion 32 will run away from port 36 towards the blind end of bore 34. However, when the centrifuge is operated, centrifugal force causes the cytofunnel arrangement to tilt about stub shafts 40 into a position in which the bore 34 is aligned along a radius of the centrifuge from the rotational axis of the latter, allowing the sample to run under centrifugal force to the end of bore 34 adjoining the glass slide, to contact the latter, and allowing cells from the sample to be deposited on the slide.

For certain applications, a sheet of absorbent paper, e.g. filter paper, may be sandwiched between plate 20 and a glass slide 12, such sheet having an aperture registering with port 36 but slightly larger than the latter, the filter paper serving to absorb excess liquid from the sample in substantially the same way as described in EP 0184374. Sealing means may be provided to improve sealing between the surface of plate portion 20 around the port 32 with respect to the glass slide. Such sealing means may, for example, take the form of an integral raised annular bead surrounding and concentric with port 36, or of a gasket or of an elastomeric sealing ring received in an annular groove formed in the face of the plate 20 around, and concentric with, port 36.

In the preferred embodiments of the invention, the plate portion 20 of the specimen funnel 14 is welded along its longitudinal edges to the adjoining portions of the side walls 18 of the slide holder 10, for example ultrasonically, by means of an ultrasonic welding head (not shown) which also serves to hold the specimen funnel 14 in place on the slide holder 10, with the slide 12 disposed therebetween. As illustrated in FIG. 4, such welding is preferably effected in such a way as effectively to tack-weld the longitudinal edges of plate 20 to the walls 18, i.e. to weld the plate 20 to the walls 18 only at a limited number of isolated locations, to make subsequent separation of the specimen funnel from the slide holder relatively easy.

As illustrated in FIG. 5, a tear wire 50 may be incorporated in the welded joint between each longitudinal edge of the plate 20 and the adjoining side wall 18, such tear wire terminating in a tear-tab accessible to the user, so that when it is desired to separate the specimen funnel 14 from the slide holder 10 after cytocentrifugation, the user can simply grasp the tear tab 52 and pull to sever the weld between the plate 20 and the slide holder to allow separation of the specimen funnel from the slide holder. In the arrangement illustrated in FIG. 5, a single tear tab 52 is connected to the ends of two tear wires 50, each incorporated in the weld between a respective longitudinal edge of the plate 20 and the slide holder, but it will be appreciated that, if desired, a separate tear tab may be provided for the tear wire 5 on each side. Instead of welding the specimen funnel 14 to the slide holder 10 ultrasonically, these components may be welded together by passing an electric current through a wire which extends between each longitudinal edge of the plate 20 and the opposing surface of the adjoining side wall 18 of the slide holder, thereby to fuse the plastics material of the plate 20 and the slide holder 10 together and at the same time incorporating the electrical resistance heating wire in the weld, so that the latter can serve as the tear wire for subsequent separation of the welds when it is desired to separate the specimen funnel 14 from the slide holder 10.

It will be understood that, whilst it is preferred to weld the specimen funnel 14 to the slide holder 10, these two components may be held together in some other way, for example by integral clip formations which are so designed as to prevent nondestructive disengagement of the formation, thereby ensuring that the cytofunnel arrangement can be used only once, or these components may simply be held together by an appropriate adhesive. (In these variants, the specimen funnel and slide holder may be of thermosetting plastics instead of thermoplastics, since no welding may be necessary). Other variations are, of course, possible. Thus, for example, the slide holder 10 and the specimen funnel 14 might be moulded as a single integer with the plate 20, for example, being connected along one edge thereof by an integral flat hinge with the slide holder 10, allowing the specimen funnel 14 to be folded over onto the slide holder after location of the slide and prior to permanent securing of the specimen funnel 14 to the slide holder.

FIGS. 4 and 5 show the cross sectional area of the fused material. The cross section is designed to be strong in compression and torsion but weak in peel, to allow for easy removal of the slide after centrifuging.

What is claimed is:

1. A cytofunnel arrangement comprising a specimen funnel, a slide and a slide holder, the slide holder being integrally connected with the specimen funnel to form a unit and being adapted for destructive separation from the specimen funnel along predetermined lines or regions to allow extraction of the slide undamaged, whilst preventing re-use of the specimen funnel and slide holder, a separation filament being incorporated between the specimen funnel and the slide holder and terminating in tab means which can be gripped and pulled to pull the separation filament from the unit in such a way as to divide the slide holder from the specimen funnel, and wherein said separation filament is an electrical resistance wire which has been used to weld the specimen funnel and the slide holder together by passing current through the wire to heat the same and thus effect said welding by electrofusion welding.

2. A cytofunnel arrangement according to claim 4 wherein said slide holder and specimen funnel are of thermoplastics material and are welded together with said slide in position in the holder.

3. A cytofunnel arrangement according to claim 1, wherein said specimen funnel and said slide holder have been welded together ultrasonically.

* * * * *

UNITED STATES PATENT AND TRADEMARK OFFICE
CERTIFICATE OF CORRECTION

PATENT NO. : 6,162,401
DATED : December 19, 2000
INVENTOR(S) : Karl J. Callaghan It is certified that error appears in the above-identified patent and that said Letters Patent is hereby corrected as shown below:

Title page,
Under "FOREIGN PATENT DOCUMENTS", add the following omitted patents:
| | | |
|---|---|---|
| -- 0,047,840 B1 | 3/1985 | European Pat. Off. |
| GB 2,184,837 A | 7/1987 | United Kingdom |
| GB 2,243,448 B | 4/1994 | United Kingdom |
| 0,205,107 A2 | 12/1986 | European Pat. Off. |
| WO 95/17938 | 7/1995 | PCT |
| 55,131958 | 10/1980 | Japan --. |

Column 2,
Line 15, change "13", to read -- 10 --.

Column 4, claim 2,
Line 59, change "4", to read -- 1 --.

Signed and Sealed this

Ninth Day of October, 2001

*Attest:*

NICHOLAS P. GODICI
*Attesting Officer*    *Acting Director of the United States Patent and Trademark Office*